United States Patent
Ravussin

(10) Patent No.: US 8,034,091 B2
(45) Date of Patent: Oct. 11, 2011

(54) METHOD FOR THE ABLATION OF CARTILAGE TISSUE IN A KNEE JOINT USING INDOCYANINE

(75) Inventor: Pierre Ravussin, Belmont (CH)

(73) Assignee: LASERIX sarl, Neuchâtel (CH)

( * ) Notice: Subject to any disclaimer, the term of this patent is extended or adjusted under 35 U.S.C. 154(b) by 217 days.

(21) Appl. No.: 11/760,250

(22) Filed: Jun. 8, 2007

(65) Prior Publication Data
US 2008/0306574 A1 Dec. 11, 2008

(51) Int. Cl.
*A61N 5/067* (2006.01)
*A61B 18/28* (2006.01)

(52) U.S. Cl. .............. 607/89; 128/898; 606/15
(58) Field of Classification Search ............... 606/2–19; 128/898; 607/88–94
See application file for complete search history.

(56) References Cited

U.S. PATENT DOCUMENTS

| | | | |
|---|---|---|---|
| 4,905,247 A | 2/1990 | Glessner et al. | |
| 5,464,436 A * | 11/1995 | Smith | 607/89 |
| 5,514,130 A * | 5/1996 | Baker | 606/41 |
| 5,582,190 A * | 12/1996 | Slavin et al. | 128/898 |
| 5,942,534 A * | 8/1999 | Trauner et al. | 514/410 |
| 6,221,068 B1 | 4/2001 | Fried et al. | |
| 6,251,100 B1 * | 6/2001 | Flock et al. | 606/2 |
| 6,628,686 B1 | 9/2003 | Sargent | |
| 7,331,954 B2 * | 2/2008 | Temelkuran et al. | 606/15 |
| 2004/0147501 A1 | 7/2004 | Dolmans et al. | |
| 2004/0186469 A1 * | 9/2004 | Woloszko et al. | 606/41 |
| 2005/0033292 A1 * | 2/2005 | Teitelbaum et al. | 606/53 |
| 2005/0187537 A1 * | 8/2005 | Loeb et al. | 606/1 |
| 2006/0084958 A1 * | 4/2006 | Raif et al. | 606/15 |
| 2006/0231107 A1 * | 10/2006 | Glickman et al. | 128/898 |
| 2007/0213792 A1 * | 9/2007 | Yaroslavsky et al. | 607/100 |
| 2007/0276359 A1 * | 11/2007 | Segal | 606/11 |

FOREIGN PATENT DOCUMENTS
WO 2004/080284 A2 9/2004

OTHER PUBLICATIONS

McNally et al. Optimal Parameters fo Laser tissue Soldering. Part I: Tensile Strength and Scanning Electron Microscopy Analysis, 1999, lasers in Surgery and medicine, 24, 319-331.*
Ageeva et al., Organic Dyes in Laser Surgery of Cartilaginous Tisses, 2007, Biomedical Engineering, 41, 69-77.*
Sherk et al., Electromagnetic Surgical Devices in Orthopaedics: Lasers and Radiofrequency, Journal of bone and Joint Surgery, Apr. 2002, 84, 675-681.*
Prodoehl, John A. et al., "308 nm Excimer Laser Ablation of Cartilage," Lasers in Surgery and Medicine 15, 1994, pp. 263-268.

(Continued)

*Primary Examiner* — Henry Johnson, III
(74) *Attorney, Agent, or Firm* — Griffin & Szipl, P.C.

(57) ABSTRACT

A method for the ablation of human or animal articular cartilage is disclosed that employs an exogenous absorber, such as a compound having the molecular formula $C_{43}H_{47}N_2NaO_6S_2$, to coat or color the surface of the articular cartilage. The coated or colored cartilage surface then has an energy absorption peak at a specific wavelength due to the exogenous absorber, which makes it possible to employ a simple and cheap laser diode to generate a pulsed laser beam at the specific wavelength so as to superheat the coated or colored cartilage thereby causing at least partial ablation of cartilage.

11 Claims, 3 Drawing Sheets

OTHER PUBLICATIONS

Marion, J.E. et al., "Medical Applications of Ultra-Short Pulse Lasers," Lawrence Livermore National Laboratory, UCRL-JC-133470 Rev 1, 1999.

Prahl, Scott, et al., "Optical Absorption of Indocyanine Green (ICG)," http://omlc.ogi.edu/spectra/icg/index.html, printed Apr. 27, 2004.

H.W. Sands Corp. "Specialty Chemicals for the World Wide Imaging Industry—Indocyanine Green," http://www.hwsands.com/snapshotpgs/indocyaninegreen.htm, printed Apr. 16, 2007.

"Arthoscopic Knee Surgery," http://www.orthopedie.com/en/meniscus/arthoscopic_knee_surger..., printed Apr. 13, 2007.

"Knee Arthoscopy," http://www.arthoscopy.com/sp05002.htm, printed Apr. 13, 2007.

"Knee Joint—Anatomy & Function," http://www.arthoscopy.com/sp05001.htm, printed Apr. 13, 2007.

"Meniscal Repair," http://www.arthoscopy.com/sp05026.htm, printed Apr. 13, 2007.

Lei S. Meng et al., High Power 7-GHz Bandwidth External-cavity Diode Laser Array and Its Use in Optically Pumping Singlet Delta Oxygen, 14 Optics Express 10469-10474 (2006), previously filed as Exhibit C.

Diederik S. Wiersma et al., A Temperature-tunable Random Laser, 414 Nature 708-709 (2001), previously filed as Exhibit D.

Gray'S Anatomy 329-338 and 346-348 (Lea & Febiger, 29th ed. 1985), previously filed as Exhibit E.

Stedman'S Medical Dictionary 1857 (1995), previously filed as Exhibit F.

Unnumbered page from H.C. Ohanian, Physics (W.W. Norton & Company, Inc. 1985), concurrently filed as Exhibit G.

H.C. Ohanian, Physics 810-812 (W.W. Norton & Company, Inc. 1985), concurrently filed as Exhibit H.

Stedman'S Medical Dictionary 3 (1995), concurrently filed as Exhibit I.

Venn, M.F., "Chemical composition of human femoral head cartilage: influence of topographical position and fibrillation," Annals of the Rheumatic Diseases, 1979, 38, 57-62, concurrently filed as Exhibit A8.

Hale, George M., et al., "Optical Constants of Water in the 200-nm to 200-μm Wavelength Region," Applied Optics, Mar. 1973, vol. 12, No. 3, 555-563, concurrently filed as Exhibit A9.

Ravussin, P. et al., "Cartilex for precise hyaline cartilage surface removal—tissue coloration combined with diode laser—a feasibility study," KTI Project—9012.1 PFLS-LS, one page, published Sep. 10, 2008, concurrently filed as Exhibit A11.

* cited by examiner

METHOD FOR THE ABLATION OF CARTILAGE TISSUE IN A KNEE JOINT USING INDOCYANINE

FIELD OF THE INVENTION

The invention pertains to a method, and system for performing the method, for the ablation of cartilage tissue in a joint, such as, for example, a knee joint, of a human or animal. More particularly, the invention pertains to a method for the ablation of cartilage tissue that utilizes an exogenous absorber applied to the surface of the cartilage tissue so as to selectively absorb electromagnetic energy from a diode laser and thereby effect ablation of cartilage tissue coated with the exogenous absorber. The present invention includes a system, including a diode laser and an exogenous absorber, for performing the method of the present invention.

BACKGROUND OF THE INVENTION

In the orthopedic arts, it is known that cartilage tissue in a joint, such as a knee joint, has to be reshaped in order to treat certain joint disorders such as a hyaline cartilage surface irregularities. Generally, arthroscopic surgery is preferred due to the lower rates of morbidity and mortality, and the shorter recovery times experienced by patients. Typically, an orthopedic surgeon will operate arthroscopically on a joint, such as the knee, by inserting one or more trocars into the joint capsule, and then through one of the trocars an arthroscope is inserted so the surgeon can visualize the tissues (i.e., synovium and cartilage) of the joint. The other trocar is used to deploy a surgical instrument, such as a mechanical cutting tool (i.e., a grasper, knife or curette). However, these mechanical cutting tools may damage a significant amount of healthy cartilage while removing damaged or diseased tissue. Because cartilage is avascular and heals slowly, there is a need to develop a tool or device that can remove damaged cartilage tissue while minimizing collateral damage to surrounding healthy cartilage.

The present inventor has considered ablation techniques involving laser technology to address this problem. For the purpose of this disclosure, "ablation" means "the act or process of ablating," and "ablating means to remove or dissipate by vaporization or melting." The ablation of cartilage using a 308 nm Excimer laser (a UV laser) in an in vitro cartilage sample is disclosed by J. A. Prodoehl et al. in "308 Excimer Laser Ablation of Cartilage," Lasers Surg. Med. 15:263-268 (1994). However, Prodoehl's article does not enable one of ordinary skill in the art to perform ablation of cartilage in vivo. Furthermore, the Excimer laser is expensive and relatively bulky so it is not suitable for use in a hospital or outpatient surgery clinical environment. While cheaper lasers that are relatively compact and light are known, such as laser diodes for example, these lasers are not suitable for arthroscopic surgical ablation of cartilage because their wavelength energies are poorly absorbed by cartilage.

Known methods for the ablation of articular cartilage using laser technology employ crystal lasers in the infrared spectrum such as Ho:YAG lasers (wavelength: 2µ) and Er:YAG lasers (wavelength: 2.9µ). However, there are several drawbacks to the application of infrared laser technology to arthroscopic surgery. First, arthroscopic surgery is performed in an aqueous environment. After entering the joint capsule with a trocar, the surgeon infuses an aqueous solution into the joint capsule so that visualization of the joint tissues with an arthroscope is optimized and to prevent excessive deterioration of the joint tissues during the procedure. Unfortunately, the aqueous liquid must be pierced by the infrared laser beam in order to reach the cartilage. In other words, the radiation of the infrared lasers must literally pierce a hole in the water by vaporizing it before reaching the cartilage to be ablated. This means that the infrared laser beam must have considerable energy, which then generates undesirable thermal effects. These undesirable thermal effects increase as the power of the laser increases, which makes quick ablation impossible without damaging a significant amount of healthy joint tissue.

A second drawback of infrared lasers relates to the difficulties encountered when selecting a laser that operates at a wavelength not absorbed well by the aqueous environment. It turns out that a laser that is not absorbed well by the aqueous environment utilized during arthroscopic surgery is also not absorbed well by articular cartilage because of the water content of articular cartilage. Therefore, there is a need to employ some means for enhancing the absorption of laser energy by damaged cartilage tissue that the surgeon wishes to ablate so that energy is preferentially absorbed by the damaged cartilage tissue and not by the healthy hyaline cartilage.

The present inventor has considered the application of an exogenous absorber, such as a dye, to enhance the absorption of laser energy by cartilage tissue to effect selective tissue ablation. However, previous applications of energy absorbing dyes to therapeutic methods have been limited. For example, U.S. Pat. No. 6,221,068 B1 to Fried et al., and incorporated herein by reference for all it discloses, discloses the use of a dye such as Indocyanine Green (ICG) mixed with albumin or fibrinogen to create a tissue "solder." ICG has an absorption peak at 810 nm when combined with albumin. The tissue solder is applied to opposing edges of a wound, and a commercially available diode laser is used to activate the tissue "solder" and "weld" the tissue edges together. However, U.S. Pat. No. 6,221,068 does not teach, or even suggest, applying the ICG/diode laser combination to effect tissue ablation. On the contrary, U.S. Pat. No. 6,221,068 pertains to using the ICG dye to heat albumin or fibrinogen applied to wound edges to create an adhesive effect. Furthermore, U.S. Pat. No. 6,221,068 does not teach or suggest that the tissue "solder" could be applied to a wound in an aqueous environment.

U.S. Patent Application Publication No. US 2004/0147501 to Dolmans et al. discloses generally "photodynamic therapy," which pertains to treatment methods employing a photosensitizer to generate reactive radical species to destroy cells in a target tissue. This publication discloses that ICG is a photosensitizer. The photosensitizer is injected into an injection site of a treatment subject and allowed to find its way into the subject's vasculature. After time, the photosensitizer accumulates in a highly vascularized or neovascularized target tissue, such as a rapidly growing tumor. A laser is then used to activate the photosensitizer to generate the radical species used to kill the target tissue. Photodynamic therapy, however, is not an ablation therapy. Furthermore, photodynamic therapy can only be applied to vascularized or neovascularized tissues, which most articular cartilage tissue (e.g., a hyaline cartilage of the knee) is not.

The present invention endeavors to provide an improved method and system for the ablation of cartilage tissue in vivo in a human or animal treatment subject that overcomes the disadvantages of prior art methods and systems. Accordingly, a primary object of the present invention is to overcome the disadvantages of the prior art methods and systems for the ablation of cartilage tissue in vivo in a human or animal treatment subject.

Another object of the present invention is to provide a method and system for the ablation of cartilage tissue that can be employed arthroscopically in an aqueous environment within the joint capsule of a living human or animal treatment subject. Another object of the present invention is to provide a method and system for the ablation of cartilage tissue that employs an economical and compact diode laser so that the method and system may be employed in a hospital and/or outpatient surgical environment.

Yet another object of the present invention is to provide a method and system for the ablation of cartilage that ablates cartilage tissue in a more efficient manner than achieved by prior art methods and systems.

SUMMARY OF THE INVENTION

In accordance with the above objectives, the present invention provides a method for the in vivo ablation of human or animal cartilage that includes the steps of: (a) applying an exogenous absorber to a portion of a surface of cartilage, wherein the exogenous absorber selectively absorbs the electromagnetic energy at a first electromagnetic energy narrow spectrum; (b) generating electromagnetic energy at a secondary electromagnetic energy far infrared wide spectrum using a laser diode; and (c) directing the electromagnetic energy generated by the laser diode at the secondary electromagnetic energy spectrum onto the exogenous absorber applied to the portion of the surface of cartilage so that the articular cartilage absorbs the secondary electromagnetic energy causing at least partial ablation of cartilage. In accordance with another method embodiment of the present invention, the previous embodiments are further modified so that the cartilage is avascular articular cartilage. In accordance with yet another method embodiment of the present invention, the articular cartilage of the previous embodiments is any joint cartilage.

In accordance with still another method embodiment of the present invention, the previous embodiments are further modified so that the electromagnetic energy generated by the laser diode is directed through a fluid contained within a joint capsule of a joint before being absorbed by the exogenous absorber, wherein the fluid comprises synovial fluid or an aqueous solution or a mixture of synovial fluid and the aqueous solution. In accordance with another method embodiment of the present invention, the previous embodiments are further modified so that the exogenous absorber is a dye that colors the portion of the surface of the cartilage when applied thereto, and the exogenous absorber comprises a compound having the following formula

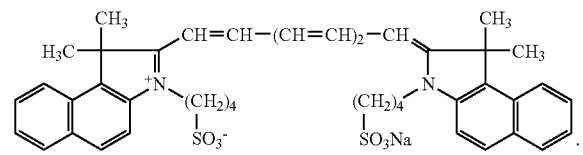

In accordance with yet another method embodiment of the present invention, the previous embodiments are further modified so that the exogenous absorber is applied to portion of the surface of articular cartilage in the form of an aqueous solution using at least one trocar inserted into a joint capsule. In accordance with still another method embodiment of the present invention, the previous embodiments are modified so that the aqueous solution is a physiological fluid comprising 0.9% sodium chloride. In another method embodiment of the present invention, the aqueous solution is phosphate buffered saline.

In accordance with another method embodiment of the present invention, the previous embodiments are further modified so that the exogenous absorber maximally absorbs electromagnetic energy at the first electromagnetic energy spectrum that is equal to, or approximately equal to, the second electromagnetic spectrum.

In accordance with the present invention, a system for ablating cartilage in a human or animal is also provided, wherein the system includes: (a) a laser diode that generates a pulsed laser beam at about a first wavelength, wherein each laser pulse generated by the laser diode lasts no more than 10 msec; (b) an optical conduit connected to transmit the pulsed laser beam generated by the laser diode; and (c) an exogenous absorber, wherein the exogenous absorber selectively absorbs electromagnetic energy at about a second wavelength so that when the exogenous absorber is applied to a surface of cartilage and is subjected to the pulsed laser beam transmitted by the optical conduit, the exogenous absorber absorbs electromagnetic energy from the pulsed laser beam and effects ablation of at least a portion of the cartilage. In accordance with another system embodiment of the present invention, the previous system embodiment is further modified so that the pulsed laser beam generated by the laser diode has a power of greater than 30 W. In accordance with yet another system embodiment of the present invention, the previous embodiments are further modified to include a laser device comprising an array of laser diodes. In accordance with still another system embodiment of the present invention, the previous embodiments are further modified to include two trocars, wherein one trocar is an irrigation trocar and the other trocar is an evacuation trocar.

In accordance with another system embodiment of the present invention, the previous embodiments are further modified so that the exogenous absorber has an electromagnetic energy absorption peak at the half wavelength of that of the laser diode. In accordance with another system embodiment of the present invention, the previous embodiments are further modified so that the first wavelength is around 785 nm.

In accordance with another system embodiment of the present invention, the previous embodiments are further modified so that the first wavelength is at a wavelength for which a non toxic dye does exist.

In accordance with still another system embodiment of the present invention, the exogenous absorber comprises a compound having the following formula

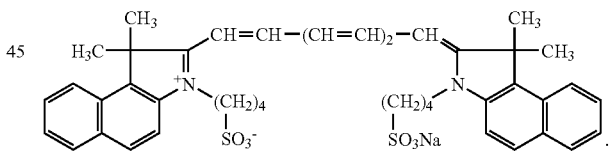

Further objects, features and advantages of the present invention will become apparent from the Detailed Description of Illustrative Embodiments, which follows, when considered together with the attached drawings.

DETAILED DESCRIPTION OF THE ILLUSTRATIVE EMBODIMENTS

The apparatus of the present invention is a system for the ablation of cartilage tissue in vivo in a human or animal treatment subject. The present invention also includes a method for the ablation of cartage tissue in vivo in a human or animal treatment subject. While the present invention is described with respect to application to ablation of cartilage of the knee joint, the present invention is not limited in application to ablation of knee joint cartilage. The present invention may be applied to the ablation of human and/or animal cartilage in other joints as well, and even to nonarticular cartilage or to any tissue that fixes the dye.

The present invention is described with reference to FIGS. 1 to 4 where like parts are referred to using like character references. In addition, a non-limiting illustrative apparatus embodiment, in accordance with the present invention, will be described first followed by a description of a non-limiting method embodiment of the invention.

Figure 1:
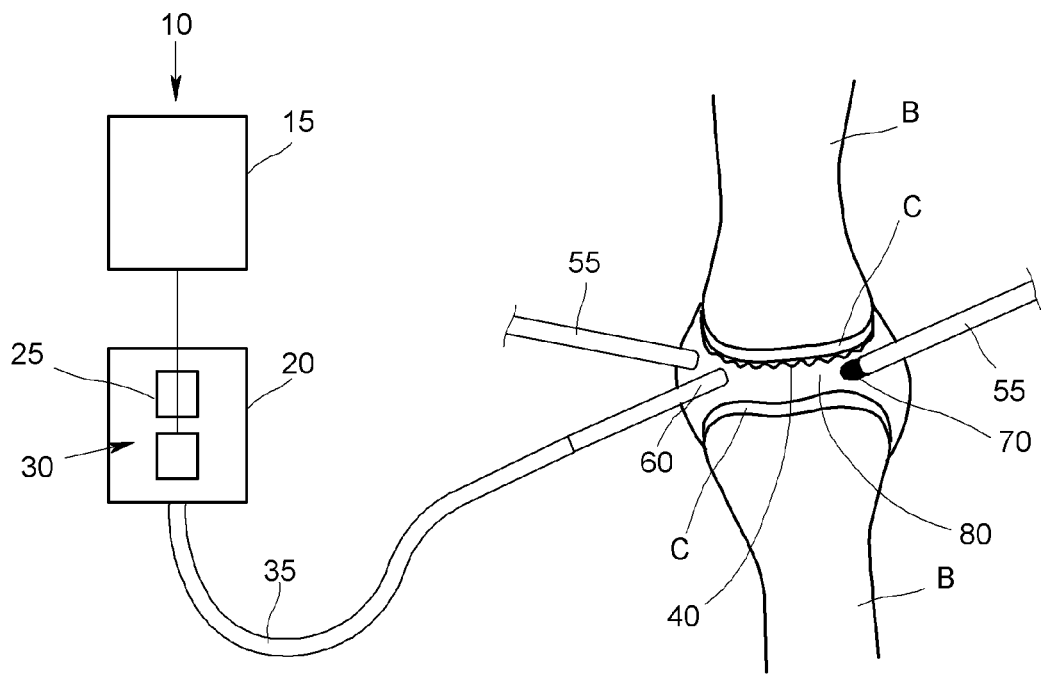
FIG. 1 is a schematic diagram of the system, in accordance with the present invention, for the ablation of cartilage tissue in vivo in a human or animal treatment subject.

A system 10 for ablating cartilage in vivo in a human or animal treatment subject includes, as shown in FIG. 1, a power source 15 connected to energize a laser device 20 that includes a laser diode 25 (or an array of laser diodes 30). The laser diode 25 (or the array of laser diodes 30) generates a pulsed laser beam having a wavelength of $\lambda_A$, wherein each laser pulse generated by the laser diode 25 (or the array of laser diodes 30) lasts no longer than about 10 msec and has a power of several hundred watts. However, the laser diode 25 (or the array of laser diodes 30) may be operated to emit a single laser pulse or a train of laser pulses. When system 10 is operated to generate a train of laser pulses (i.e., to generate a pulsed laser beam), the train of laser pulses may be adjusted in terms of duration of the train, repeat-frequency of the laser pulses, and power of the pulsed laser beam. An optical conduit 35 is connected to transmit the pulsed laser beam from the laser diode 25 (or the array of laser diodes 30) to wherever the pulsed laser beam is to be applied. Therefore, the optical conduit includes one or more flexible optical fibers for transmitting the pulsed laser beam.

The system 10 also includes an exogenous absorber that selectively absorbs electromagnetic energy at a wavelength of about $\lambda_B$, wherein either $\lambda_A = \lambda_B$, or $\lambda_A \approx \lambda_B$. An exogenous absorber 40, in accordance with the present invention, is a compound or composition that includes a chromophore or dye that absorbs radiation selectively thereby confining ablation to the immediate area where the exogenous absorber is applied to cartilage tissue. In one embodiment of the present invention, the exogenous absorber includes ICG, which is a nontoxic dye already approved for medical applications and which has an absorption peak at about 785 nm when fixed to articular cartilage. ICG has a molecular formula of $C_{43}H_{47}N_2NaO_6S_2$ and is also known by the American Chemical Society designation CAS No. 3599-32-4. The chemical structure for ICG is:

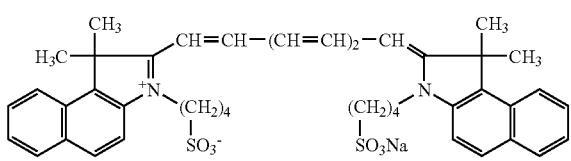

Persons of ordinary skill in the art would appreciate that other chromophores and dyes, and mixtures thereof, may be employed in the practice of the present invention so long as there is a corresponding laser diode (or laser diode network) that generates a pulsed laser beam that satisfies one of the relationships: $\lambda_A = \lambda_B$, or $\lambda_A \approx \lambda_B$.

In the case where the system 10 employs ICG, which is an exogenous absorber 40 having an absorption peak at about 785 nm, a laser diode 25 that generates a pulsed laser beam at about 785 nm is used, wherein each laser pulse generated by the laser diode lasts no more than 10 msec and has a power of up to several hundred watts. The system 10 also includes one or more trocars 50, 55 for accessing cartilage tissue to be ablated in vivo. When the exogenous absorber 40 is selectively applied to the synovial surface S covering cartilage tissue C on bone B, it coats or dyes the synovium S and/or the cartilage C. The ICG dye penetrates the synovial membrane S covering the cartilage C and penetrates to a depth of about 0.1 mm or less. Thus, when the pulsed laser beam, which comprises a train of laser pulses, is directed onto a portion of the cartilage C coated with the exogenous absorber 40, the exogenous absorber 40 selectively absorbs electromagnetic energy from the pulsed laser beam exiting tip 60 of optical conduit 35 thereby causing at least a portion of the irradiated and dyed cartilage to superheat to a temperature above the evaporation temperature of water. As a result, superheated cartilage vaporizes creating a vapor bubble. This vapor bubble creates tears in contiguous unvaporized cartilage causing a portion of the remaining unvaporized cartilage to disperse into a liquid medium surrounding the cartilage and contained within the joint capsule W.

The exogenous absorber ICG may be applied to the surface of cartilage C either as an aqueous solution or it may be applied directly using an applicator tool 70 deployed through one of the trocars 50, 55. As described above, the exogenous absorber ICG selectively absorbs energy from the pulsed laser beam transmitted by the optical conduit 35 and exiting tip 60 while any fluid 80 contained within the joint capsule W and any undyed cartilage absorb energy relatively poorly from the pulsed laser beam. In this way, the exogenous absorber 40 preferentially absorbs electromagnetic energy from the pulsed laser beam sufficient to achieve ablation of at least a portion of the surface of the cartilage C while undyed cartilage and the fluid 80 do not superheat.

Figure 2:
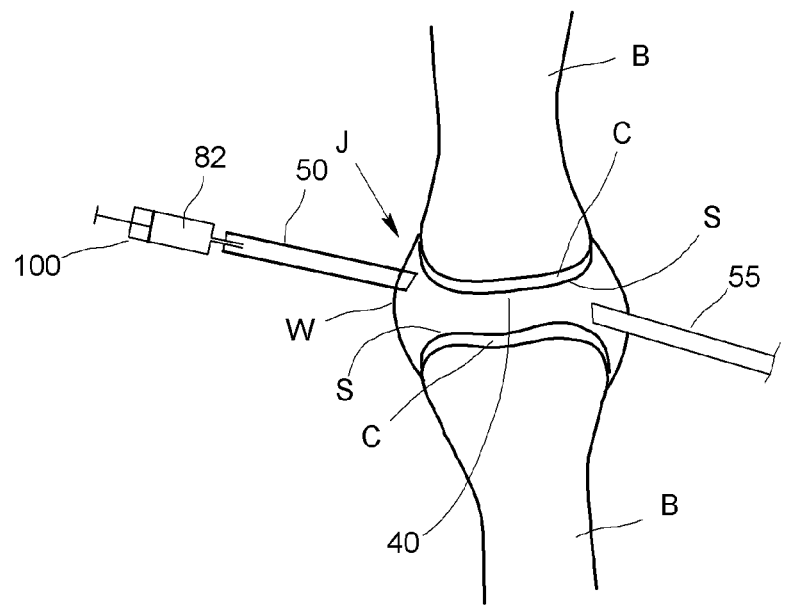
FIG. 2 illustrates the step of applying exogenous absorber to the articular cartilage of a joint.

Having described the system 10, in accordance with the present invention, a non-limiting method embodiment for the in vivo ablation of human or animal cartilage in a treatment subject will be described with reference to FIGS. 2 and 3. As shown in FIG. 2, the method includes the steps of preparing the joint J under sterile conditions and then inserting one or more trocars 50, 55 through the joint capsule W and into the inter-articular joint space. Joint J may be a knee joint or any other joint having a joint capsule. The evacuation trocar 55 is used to evacuate synovial fluid from the joint and, within seconds, the irrigation trocar 50 is used to infuse into the inter-articular space, by means of a syringe or pump 100, a fluid 82 that comprises exogenous absorber 40 in an aqueous solution such as normal saline (0.9% NaCl) or phosphate buffered saline (PBS).

In this way, exogenous absorber is applied to all of, or a portion of, the synovial surface S of cartilage C, and then is allowed to penetrate into the cartilage C. Cartilage C is generally avascular articular cartilage, although vascularized portions of articular cartilage may be ablated using the present method as well. Typically, the exogenous absorber 40 penetrates to a depth of a few tenth of mm into the cartilage C. Alternatively, exogenous absorber may be applied directly to the synovial surface S using an applicator tool 70 deployed through the trocar 50 or 55. It is beneficial to employ an exogenous absorber 40 that is a dye that colors a portion of the surface S of the cartilage C when applied thereto so the operating surgeon may arthroscopically visually verify which portions of the articular cartilage have been dyed (i.e., have had exogenous absorber successfully applied thereto) and which portions have not been dyed.

In some cases, the exogenous absorber will preferentially dye certain defects in the cartilage C, which the surgeon O intends to ablate. This preferentially dying effect has two advantages. First, when using an exogenous absorber that is a colored dye, the dying of the defects highlights the defects and aids the surgeon O in arthroscopically identifying the defects using the arthroscope 100. Second, preferential uptake of dye by cartilage defects results in a higher concentration of dye in the defects which enhances the accumulation of laser energy during ablation to areas containing defects.

As previously mentioned, the exogenous absorber may be any suitable compound or composition that selectively absorbs electromagnetic energy of a certain wavelength so that $\lambda_A = \lambda_B$, or $\lambda_A \approx \lambda_B$ such that the exogenous absorber absorbs sufficient energy to superheat dyed cartilage to the point of ablation whereas contiguous undyed cartilage does not absorb energy sufficient to superheat to the point of ablation. One particularly useful exogenous absorber comprises ICG, a compound having the following molecular formula, $C_{43}H_{47}N_2NaO_6S_2$. Suitable dyes, in addition to having a selective energy absorption spectrum, are unstable in solution so they degrade in a relatively short time. Furthermore, suitable dyes and their degradation byproducts must be nontoxic and capable of being eliminated by the treatment subject's body.

Figure 3:
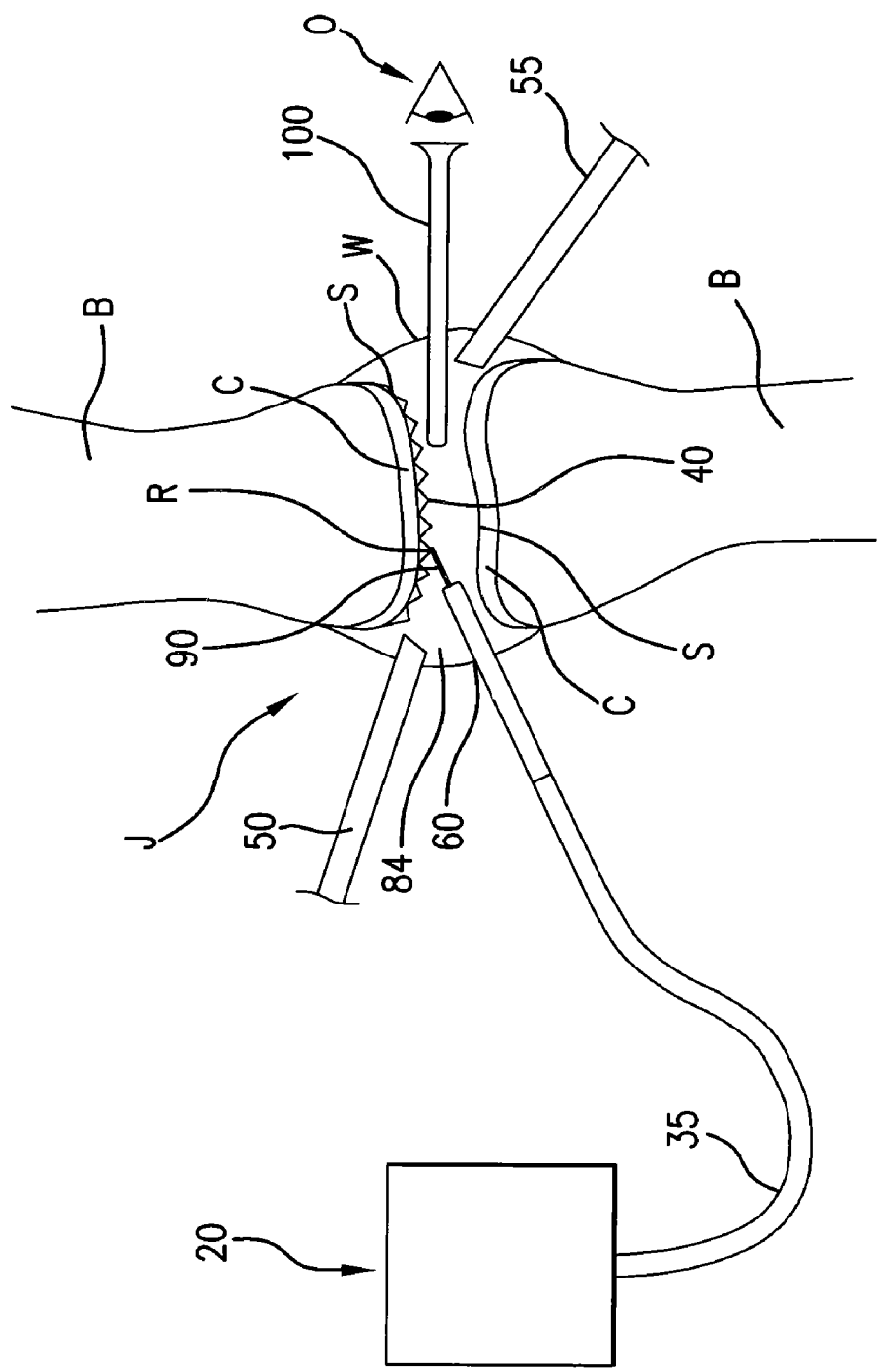
FIG. 3 illustrates the step of generating electromagnetic energy using a laser diode and directing the pulsed laser beam generated by the laser diode onto the exogenous absorber applied to a portion of the cartilage surface so that the exogenous absorber selectively absorbs electromagnetic energy causing at least partial ablation of the surface of cartilage.

As shown in FIG. 3, the method includes a step of evacuating the dye-containing fluid 82 via the evacuation trocar 55 and replacing it with a physiologic aqueous solution such as normal saline, PBS or lactated ringer's solution 84 using irrigation trocar 50. This step is carried out because the dye-containing fluid 82 is opaque to the pulsed laser beam and would selectively absorb energy and vaporize. On the other hand, the fluid 84 is used to prevent deterioration of the cartilage C during the procedure, to provide good visualization during arthroscopy, and to provide a medium through which the pulsed laser beam 90 may travel without absorbing sufficient energy from the beam 90 to vaporize. In other words, during the method of the present invention, the wavelength $\lambda_A$ of the pulsed laser beam is chosen so that it does not readily superheat and vaporize the laser transmitting fluid 84. Laser transmitting fluid 84 is selected because it is transparent to the pulsed laser beam 90.

Once dye application fluid 82 has been replaced with laser transmitting fluid 84, the surgeon O deploys the tip 60 of the optical conduit 35 through the joint capsule W, and then energizes the laser device 20 so that the laser diode (or laser diode network/array) generates electromagnetic energy (i.e., pulsed laser beam) at a first electromagnetic energy spectrum $\lambda_A$. The surgeon directs the pulsed laser beam 90 generated by the laser device 20 onto exogenous absorber previously applied to at least a portion of the surface S of cartilage C. The exogenous absorber, having peak absorption at $\lambda_B$, then selectively absorbs electromagnetic energy from the pulsed laser beam 90 thereby causing localized superheating and at least partial ablation R of cartilage C. This ablation step may be repeated on the same or other portions of the cartilage C still coated with exogenous absorber.

To further decrease the risk of collateral thermal damage to cartilage during ablation therapy, the surgeon O may irrigate the inter-articular joint space with additional fluid 84 using irrigation trocar 50 while evacuating some of the fluid 84 using evacuation trocar 55. In this way, the surgeon may flush the inter-articular joint space with fluid 84 thereby dissipating excess heat and removing debris generated by the laser ablation procedure.

Persons of ordinary skill in the art would appreciate that when an applicator tool 70 is used to apply the exogenous absorber, then use of dye application fluid 82 may be omitted altogether or applied as a pretreatment. The method of the present invention may also be practiced without first evacuating the synovial fluid. In such a case, the laser transmitting fluid 84 may comprise synovial fluid, or an aqueous solution, or a mixture of synovial fluid and an aqueous solution.

Figure 4:
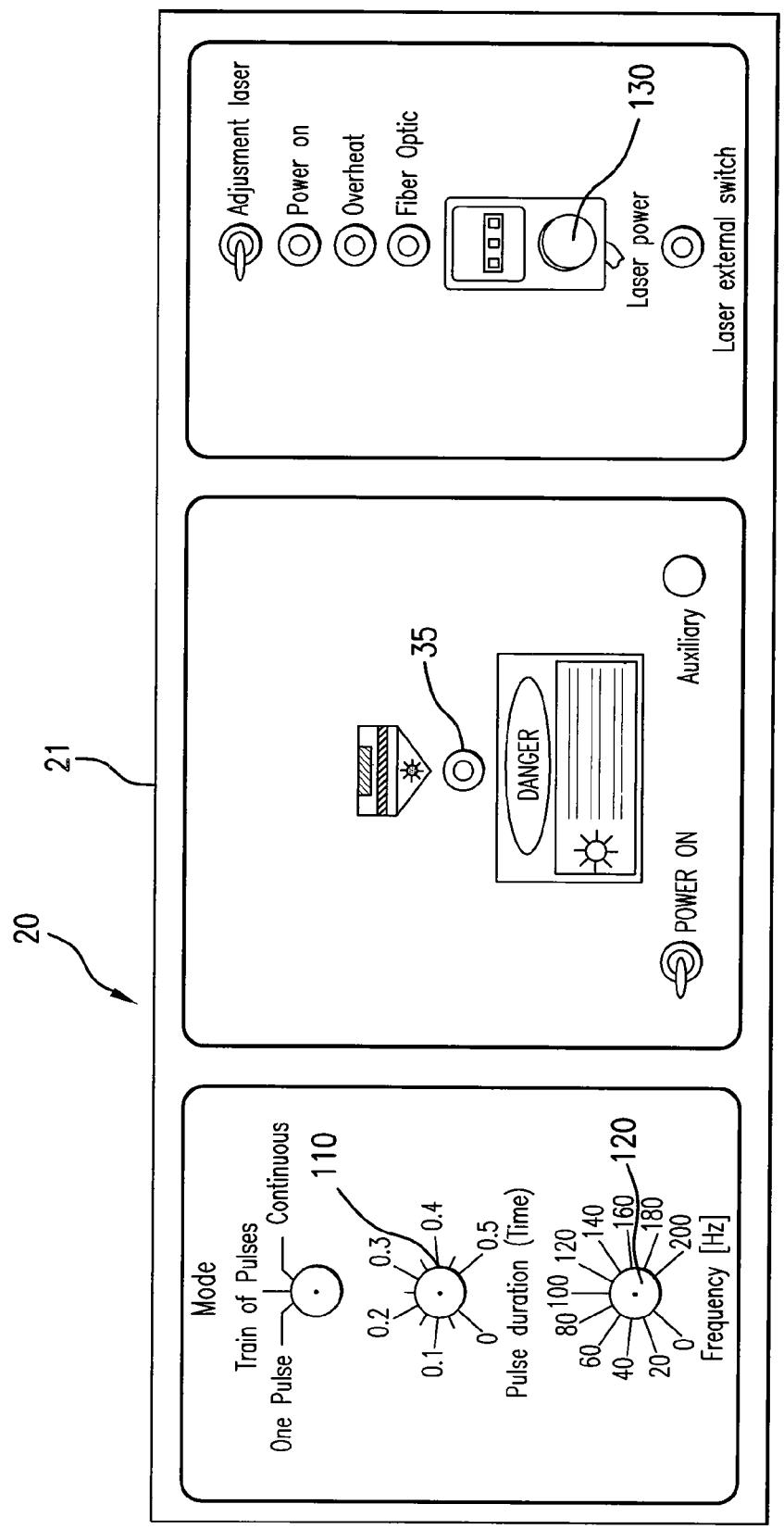
FIG. 4 illustrates an operating panel of a laser device that may be employed in accordance with the present invention.

Persons of ordinary skill in the art would also appreciate that the duration, power, and repeat-frequency of laser pulse trains may be adjusted to suit the particular type of articular cartilage (i.e., human cartilage, horse cartilage, dog cartilage, etc.) to be ablated. For example, operating panel 21 of the laser device 20 may be provided with vernier scale switches 110, 120 as shown in FIG. 4 so ablation parameters may be adjusted and optimized. For example, vernier scale switch 110 serves to adjust the duration of laser pulse trains generated by the laser diode 25 (or diode network 30). Vernier scale switch 120 serves to adjust the repeat-frequency of the laser pulse trains. Vernier scale switch 130 serves to adjust the laser power of the pulsed laser beam and the laser pulse trains.

While the present invention has been described with reference to certain illustrative embodiments, one of ordinary skill in the art will recognize, that additions, deletions, substitutions and improvements can be made while remaining within the scope and spirit of the invention as defined by the appended claims.

What is claimed is:

1. A method for the in vivo ablation of human or animal cartilage, the method comprising the steps of:
   (a) applying an exogenous absorber to a portion of a surface of cartilage, wherein the exogenous absorber selectively absorbs electromagnetic energy at a first electromagnetic energy spectrum;
   (b) deploying an optical conduit for directing electromagnetic energy through a joint capsule of a human or animal;
   (c) generating electromagnetic energy at a second electromagnetic energy spectrum using a laser diode; and
   (d) using the optical conduit to direct the electromagnetic energy generated by the laser diode at the second electromagnetic energy spectrum onto the exogenous absorber applied to the portion of the surface of cartilage so that the exogenous absorber selectively absorbs electromagnetic energy causing at least partial ablation of cartilage.

2. A method as recited by claim 1, wherein the cartilage is avascular articular cartilage.

3. A method as recited by claim 2, wherein the articular cartilage is knee joint cartilage.

4. A method as recited by claim 2, wherein the electromagnetic energy generated by the laser diode is directed through a fluid contained within a joint capsule of a joint before being absorbed by the exogenous absorber, wherein the fluid comprises synovial fluid or an aqueous solution or a mixture of synovial fluid and the aqueous solution.

5. A method as recited by claim 1, wherein the exogenous absorber is Indocyanine Green, a dye that colors the portion of the surface of the cartilage when applied thereto.

6. A method for the in vivo ablation of human or animal cartilage, the method comprising the steps of:
   (a) applying an exogenous absorber to a portion of a surface of cartilage, wherein the exogenous absorber selectively absorbs electromagnetic energy at a first electromagnetic energy spectrum, and wherein the cartilage is avascular articular cartilage and the exogenous absorber is applied to the portion of the surface of articular cartilage in the form of an aqueous solution using at least one trocar inserted into a joint capsule of a human or animal;

(b) deploying an optical conduit for directing electromagnetic energy through the joint capsule;

(c) generating electromagnetic energy at a second electromagnetic energy spectrum using a laser diode; and (d) directing the electromagnetic energy generated by the laser diode at the second electromagnetic energy spectrum using the optical conduit onto the exogenous absorber applied to the portion of the surface of cartilage so that the exogenous absorber selectively absorbs electromagnetic energy causing at least partial ablation of cartilage.

7. A method as recited by claim 6, wherein the aqueous solution is phosphate buffered saline and the exogenous absorber.

8. A method as recited by claim 6, wherein the aqueous solution is a physiological fluid comprising 0.9% sodium chloride and the exogenous absorber.

9. A method as recited by claim 6, wherein the first electromagnetic energy spectrum of the exogenous absorber has an absorption peak at about 785 nm, and the laser diode generates the second electromagnetic energy spectrum at about 785 nm.

10. A method as recited by claim 9, wherein each laser pulse generated by the laser diode lasts no more than 10 msec and has a power of up to several hundred watts.

11. A method as recited by claim 1, wherein the exogenous absorber selectively absorbs electromagnetic energy causing superheating that causes the at least partial ablation of cartilage.

* * * * *